United States Patent
Winslow et al.

(10) Patent No.: US 8,157,866 B2
(45) Date of Patent: Apr. 17, 2012

(54) METHOD AND APPARATUS FOR PERFORMING A LESS INVASIVE SHOULDER PROCEDURE

(75) Inventors: Nathan A. Winslow, Warsaw, IN (US); Paul E. Schwartz, Palo Cedro, CA (US)

(73) Assignee: Biomet Manufacturing Corp., Warsaw, IN (US)

( * ) Notice: Subject to any disclaimer, the term of this patent is extended or adjusted under 35 U.S.C. 154(b) by 277 days.

(21) Appl. No.: 11/934,917

(22) Filed: Nov. 5, 2007

(65) Prior Publication Data

US 2009/0118837 A1 May 7, 2009

(51) Int. Cl.
*A61F 2/40* (2006.01)

(52) U.S. Cl. .............. 623/19.14; 623/19.11; 623/19.12; 623/19.13

(58) Field of Classification Search ..... 623/19.11–19.14
See application file for complete search history.

(56) References Cited

U.S. PATENT DOCUMENTS

| | | | |
|---|---|---|---|
| 3,979,778 A | 9/1976 | Stroot | |
| 4,206,517 A | 6/1980 | Pappas et al. | |
| 5,282,865 A | 2/1994 | Dong | |
| 5,358,526 A | 10/1994 | Tornier et al. | |
| 5,489,309 A * | 2/1996 | Lackey et al. | 623/19.14 |
| 5,702,486 A | 12/1997 | Craig et al. | |
| 5,910,171 A | 6/1999 | Kummer et al. | |
| 6,193,758 B1 | 2/2001 | Huebner | |
| 6,197,062 B1 | 3/2001 | Fenlin | |
| 6,494,913 B1 | 12/2002 | Huebner | |
| 6,514,287 B2 | 2/2003 | Ondrla et al. | |
| 6,589,282 B2 | 7/2003 | Pearl | |
| 6,719,799 B1 * | 4/2004 | Kropf | 623/19.14 |
| 6,863,690 B2 | 3/2005 | Ball et al. | |
| 6,942,699 B2 * | 9/2005 | Stone et al. | 623/19.14 |
| 2005/0043805 A1 * | 2/2005 | Chudik | 623/19.14 |

* cited by examiner

*Primary Examiner* — Eduardo C Robert
*Assistant Examiner* — Joshua Levine
(74) *Attorney, Agent, or Firm* — Harness, Dickey

(57) ABSTRACT

A method and apparatus of performing a procedure relative to the glenohumeral joint. Resection of the glenoid and/or the humerus can proceed through an incision formed near the glenohumeral joint. The incision can be formed generally near a superior-lateral portion near the glenohumeral joint and allow less invasive access to the glenohumeral joint and the portions that form the glenohumeral joint. A stem is positioned into a resected humerus through the incision. A humeral head is coupled to the stem within the incision after the stem has been coupled to the patient's humerus.

22 Claims, 12 Drawing Sheets

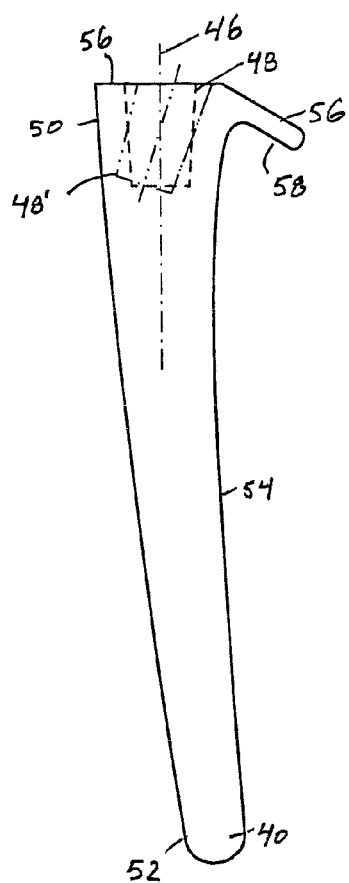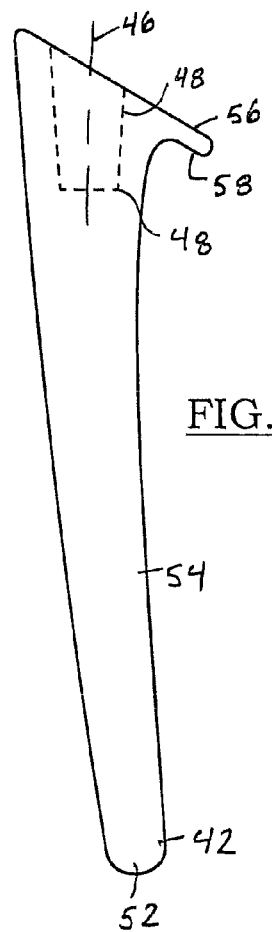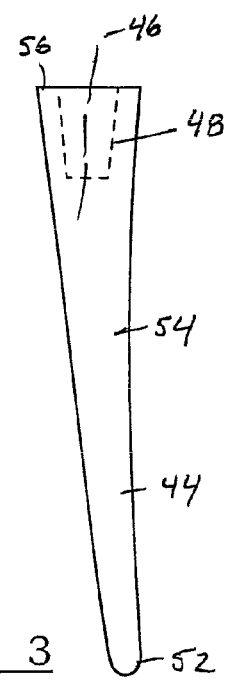
FIG. 1
FIG. 2
FIG. 3

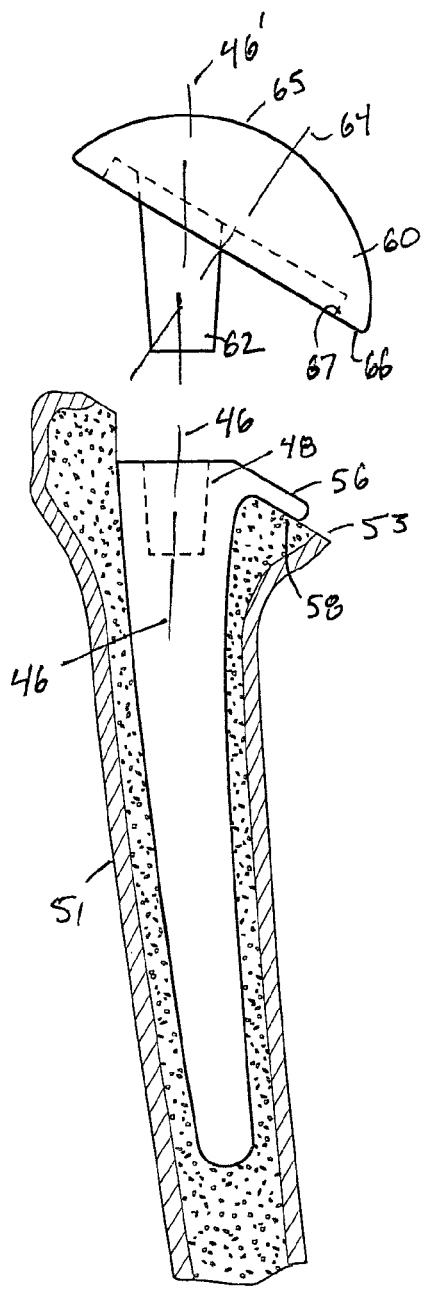
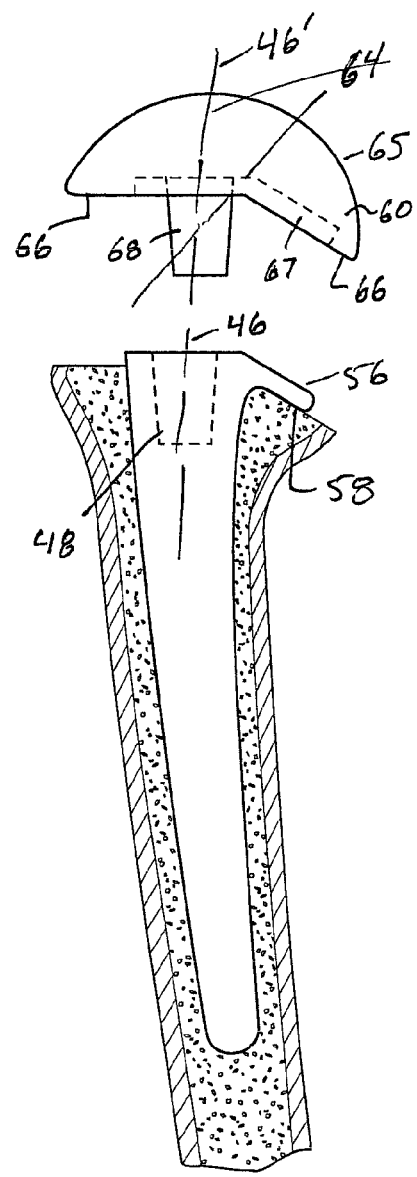
FIG. 4
FIG. 5

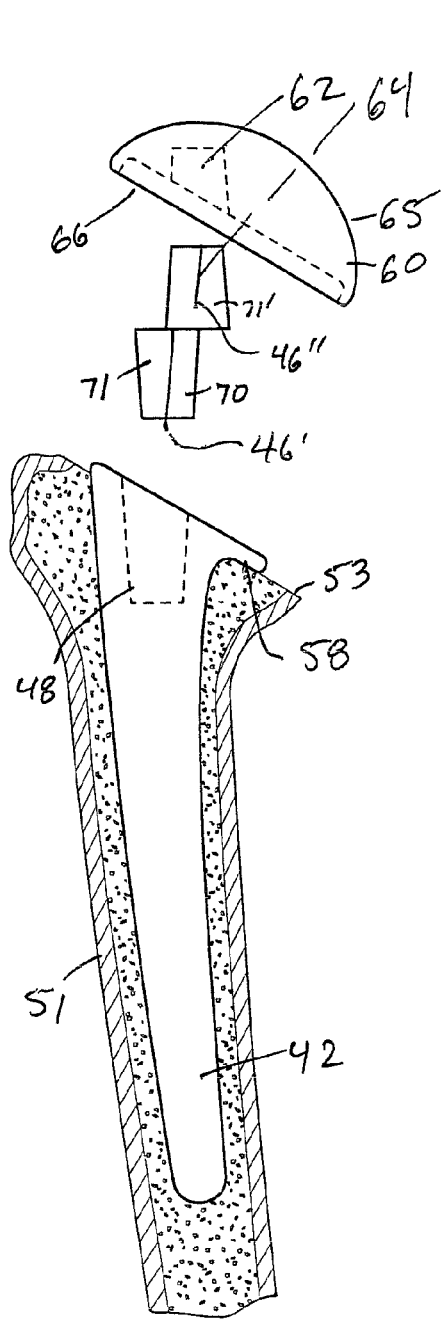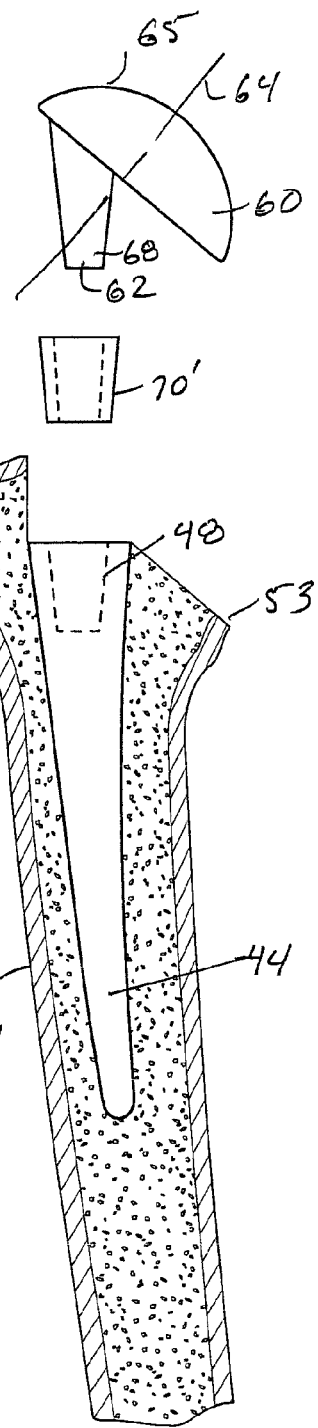
FIG. 6
FIG. 7

METHOD AND APPARATUS FOR PERFORMING A LESS INVASIVE SHOULDER PROCEDURE

FIELD

The teachings herein are directed towards an orthopedic procedure, and particularly to a less invasive orthopedic procedure relating to the shoulder.

BACKGROUND

An anatomy, such as a human anatomy, includes various articulations, soft tissues, and hard tissues to perform various functions. Generally, these functions are carried out pain-free and with a substantial range of motion. Nevertheless, various functions may deteriorate over time as soft tissue or hard tissue deteriorates and articulations deteriorate. At a selected time, various portions of the anatomy may be replaced with artificial portions to restore substantially normal or anatomical motion and functionality.

For example, the articulation of the humerus with the glenoid (the glenohumeral or shoulder joint) may deteriorate. The humeral head or the glenoid may deteriorate and become rough or lose their anatomical shapes and reduce motion, increase pain, or the like. This may happen for various reasons, such as injury, disease, or lack of motion. This may lead to replacement of the selected portions of the anatomy with a prosthesis to achieve a substantially normal or anatomical range of motion.

Although it is known to replace various portions of the anatomy, such as a humeral head and a glenoid, many procedures generally require large incisions through soft tissue. Further, various procedures require that many muscle and muscle attachments be cut to achieve access to selected portions of the anatomy. Although it may be selected or necessary to perform many procedures in this manner, it may also be desirable to achieve a less invasive procedure.

Further areas of applicability of the present teachings will become apparent from the description provided hereinafter. It should be understood that the description and various examples, while indicating various embodiments, are intended for purposes of illustration only and are not intended to limit the scope of the teachings.

SUMMARY

A less invasive or minimally invasive procedure to achieve access to the articulation region, and the capsule surrounding the humeral head and the glenoid, to allow for replacement of at least one of the glenoid or the humeral head. The procedure can be performed by accessing the rotator cuff capsule by an incision near the shoulder and separating various muscle bundles and then incising the capsule. The procedure may be performed without substantial removal or resection of the subscapularis muscle or its attachment near the glenohumeral joint. Also other muscles forming the rotator cuff can remain intact as well. A prosthetic is then configured to be inserted into and assembled within the incision.

According to various embodiments a method of performing an arthroplasty on at least one of a glenoid or a humeral head of a humerus through soft tissue of an anatomy is disclosed. According to various embodiments of the method an incision is formed in the soft tissue near a superior-lateral portion of the glenohumeral joint and portions of the deltoid muscle are separated substantially superior and lateral of the glenohumeral joint. The humeral head can be resected and a prosthetic stem is inserted into the intramedullary canal. After insertion, the humeral head can be positioned onto the stem to replace the resected humeral head. Also, the glenoid can be prepared and a glenoid implant can be inserted into the prepared glenoid. The separated muscle tissue and the incision in the soft tissue can be closed. The rotator cuff muscles, including the subscapularis muscle can remain substantially or completely connected during the arthroplasty procedure.

Further, various prosthetics are provided that allow for ease of accessing the anatomical portions and performing the less invasive procedure. For example, stems having a fixation mechanism allowing a superior approach to implant the stem, according to various embodiments, can be provided that interconnect with selected portions. Additionally, humeral heads having coupling members which have a central axis that are not perpendicular to a head interface surface can be used in the afore mentioned approach. Various prosthetic insertion methods are disclosed using these prosthetics to achieve the desired arthroplasty.

BRIEF DESCRIPTION OF THE DRAWINGS

The present teachings will become more fully understood from the description and the accompanying drawings, wherein:

FIGS. 1-3 represent alternate prosthetic stems according to the teachings of the present invention;

FIGS. 4 and 5 represent the implantation of the stem shown in FIG. 1 into a resected humerus;

FIGS. 6 and 7 represent cross sections of a resected humerus with implanted stems according to FIGS. 2 and 3 with associated alternate prosthetic coupling mechanisms;

DETAILED DESCRIPTION OF VARIOUS EMBODIMENTS

Figure 8:
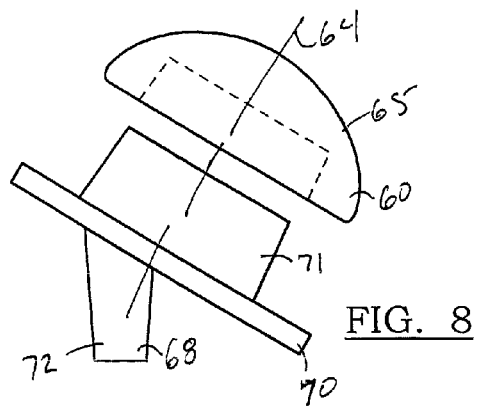
FIGS. 8-11 represent alternate humeral head fixation adaptors.

The following description of various embodiments is merely exemplary in nature and is in no way intended to limit the teachings herein, its application, or uses. Although the following description is discussed specifically for performing a procedure of a shoulder of the human anatomy, it will be understood that the procedure and instruments described herein may be augmented and used for various other procedures or in other anatomies. Therefore, although the following description is related to a shoulder procedure, it will be understood that the teachings herein are not so limited.

FIGS. 1-3 represent alternate stem prosthetics according to the teachings of the present invention. The stems 40, 42 and 44 have a defined central stem axis 46, which as described below generally corresponds to the central axis of a humeral medullary canal. The stem 40 has a locking mechanism 48 shown as a female locking taper formed on the stem proximal end 50. Additionally defined on the proximal end 50 is an optional head supporting surface 56 and a humeral engaging surface 58. The locking mechanism 48 is generally parallel to and can be co-axial with the central stem axis 46.

The stems 40, 42 and 44 are configured to be implanted into a humeral medullary canal prior to the coupling of the stem 40 to a humeral head 60. The stem 40 is implanted into the canal by applying impact forces along the central axis 46. This direction is independent of the angle of the head coupling surface 56. As described below, the stem 40 is configured to accept the humeral head 60 after the stem 40 has been implanted into the patient. This allows a significant reduction in the size of the needed incision in the subscapularis muscle.

As shown in FIGS. 4-7, the prosthetic has a humeral head 60 with a coupling mechanism 62. The coupling mechanism 62 can be a male locking taper configured to couple with the female locking taper 48 within the proximal end 50 of the stem 40, 42 and 44. The coupling mechanism 62 has a central stem axis 46', while a head axis 64 defines a head articulating surface 65. The head 60 has a stem bearing surface 66 opposite the articulating surface 65, and an optional recess area 67. The stem bearing surface 66 can be generally flat or can be multi-surfaced as is shown in FIG. 5.

The central stem axis 46' is angularly offset from the head axis 64. The stem can be offset between 0 and 55 degrees. Optionally, the central stem axis 46' is generally not perpendicular to the stem bearing surface 66. In the multi-surfaced bearing shown in FIG. 5, it is envisioned one of the bearing surfaces can be generally perpendicular to the central stem axis 46'. The central stem axis 46' is intended to be aligned with the stem central axis 46.

As shown in FIGS. 6 and 7, the head 60 can be coupled to the stem 40, 42, 44, using an intermediate coupling member 70 and a superior surgical approach. The intermediate coupling member 70 can be formed of a pair of male locking tapers 70 and 70'. These male locking members 70 and 70' define central axis 46' and 46'' which are offset to the coupling member axis 46. The offset axis function to allow a physician to adjust the positions of the head 60 with respect to the central stem axis 46 to improve mobility of the joint. The head 60 can be positioned less than about 2 mm from the stem 40, and assembled insitu.

Figure 12:
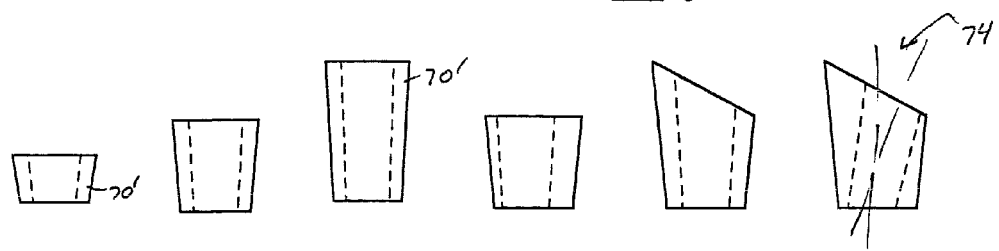
FIG. 12 represents a set of humeral head offsets.

As shown in FIGS. 7 and 12, the intermediate coupling member 70 can take the form of an annular cylindrical displacement member 70'. The displacement member 70' defines internal and external locking taper surfaces. These surfaces are configured to couple to the female coupling taper 48 in the stem 50, and the stem 62 of the head 60. Optionally, the internal locking taper can angularly or transversely adjust the position of the head 60.

Figure 9:
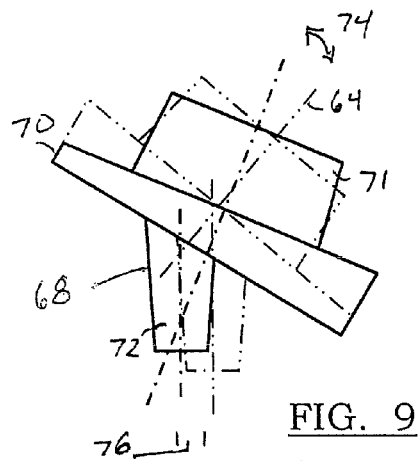
Figure 10:
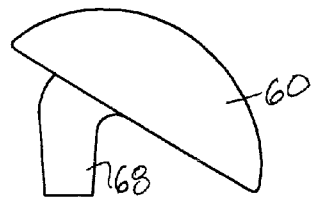
Figure 11:
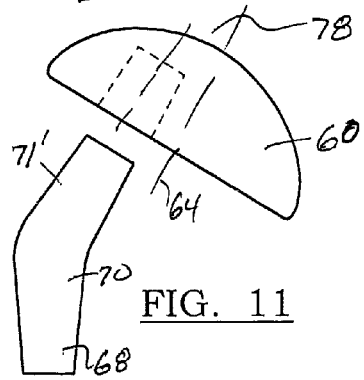

FIGS. 8-13 represent coupling members that are configured to couple the head 60 to the stem 50. As shown in FIGS. 8 and 9, the internal coupling members 70 can have coupling stems 68 that are configured to be parallel to the central axis 46 of the stem 40. Additionally, the coupling mechanisms can have a second coupling member 71 which is parallel to the head central axis 64. As shown in FIG. 9, the axis of the coupling member 71 can be angled 74 so as to adjust the angular displacement of the head 60 with respect to the central axis 46.

Figure 13:
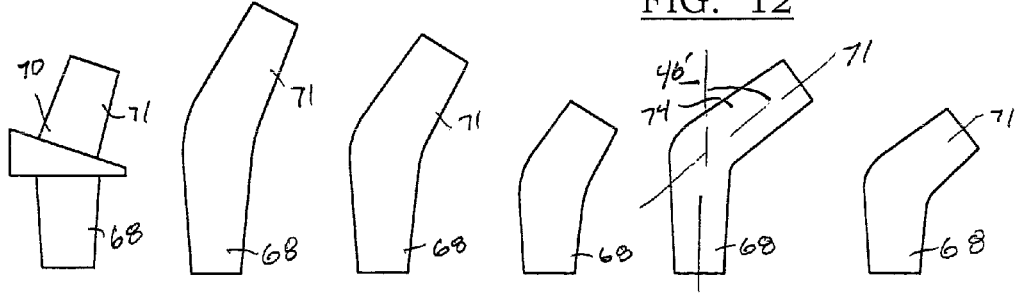
FIG. 13 represents a set of angled humeral head fixation members.

FIGS. 12 and 13 represent a kit of adaptor members 70 and 70'. As additionally shown in FIG. 7, the adaptors 70' can be used to change the displacement of the head 60 from the head supporting surface 56. FIG. 13 represents a kit of adaptors 70 each having a pair of coupling tapers 68 and 71'. The tapers are of varying lengths and coupling angles 74. The adaptors 70 can be coupled to the head 60 prior to the coupling of the head 60 to the stem 40.

Figure 14A:
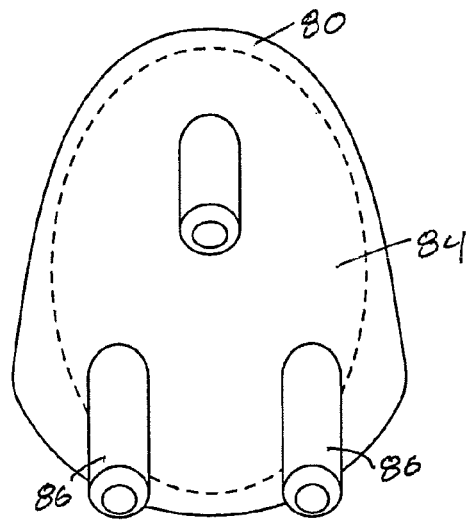
FIGS. 14a and 14b represent a glenoid according to one embodiment.
Figure 14B:
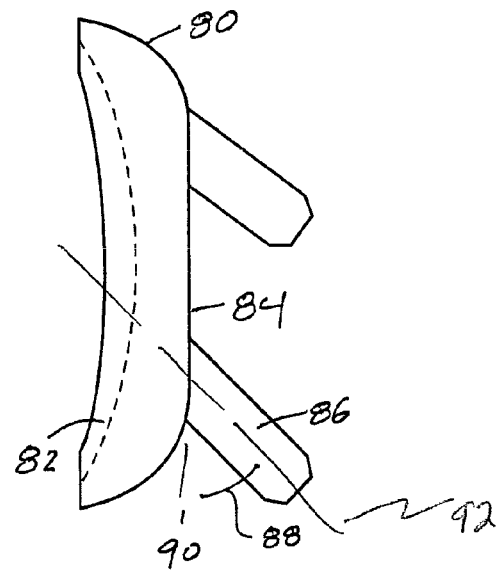

FIGS. 14a and 14b represent rear and side view of a glenoid prosthetic 80 configured to be used in a joint arthroplasty as described below. The glenoid prosthetic 80 has a curved bearing surface 82 and generally flat bearing surface 84. The bearing surface 84 is configured to be coupled to a resected glenoid and has a plurality of coupling pegs 86. The coupling pegs 86 have a plurality of intersecting axis 92 which are a predetermined angle 88 from the plane 90 which defines the bearing surface 84. The predetermined angle 88 can be between about 100 to about 60 degrees, and preferably between about 30 to about 45 degrees. The glenoid 80 and associated fixation pegs 86 are configured to allow the insertion of the glenoid 80 using a superior approach through an incision to the resected glenoid.

Figure 15:
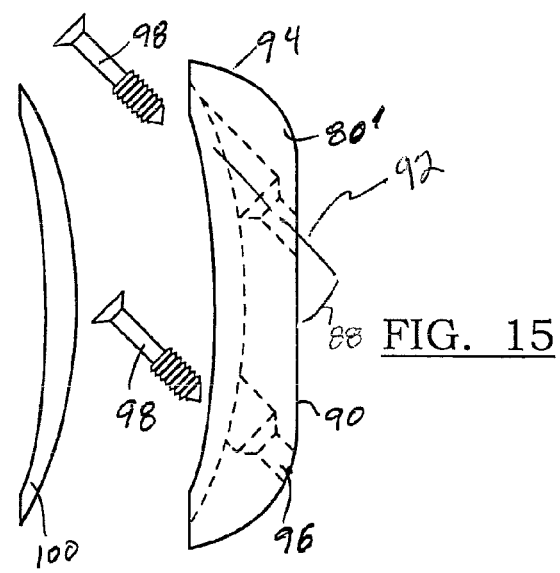
FIG. 15 represents an alternate glenoid.

As shown in FIG. 15, the glenoid 80' can take the form of a metallic base 94 and a polymer bearing member 100. The base 94 is coupled to the resected glenoid using bone coupling screws 98. The screws 98 are configured to be driven through a plurality of bone screw accepting apertures 96. The apertures 96 are angled 88 in a manner which allows for access through the superior approach.

Various instruments can be used in performing a selected procedure, such as a shoulder arthoplasty. It will be understood that various instruments and procedures may be used to perform a hemi-arthoplasty, such as replacement of only one of a humeral head or a glenoid. A total arthoplasty can be the replacement of a humeral head and a glenoid where the humeral head and the glenoid can articulate with one another after implantation.

Described below and illustrated in FIGS. 16a-19 is a procedure performed relative to a human anatomy 300. It will be understood that the following method is merely exemplary and is not intended to limit the scope of the above-described instruments. Similarly, the procedure herein is exemplary of a procedure that may be performed relative to a selected portion of the anatomy and, although a shoulder procedure is described, it is not intended to limit the teachings herein.

Figure 16:
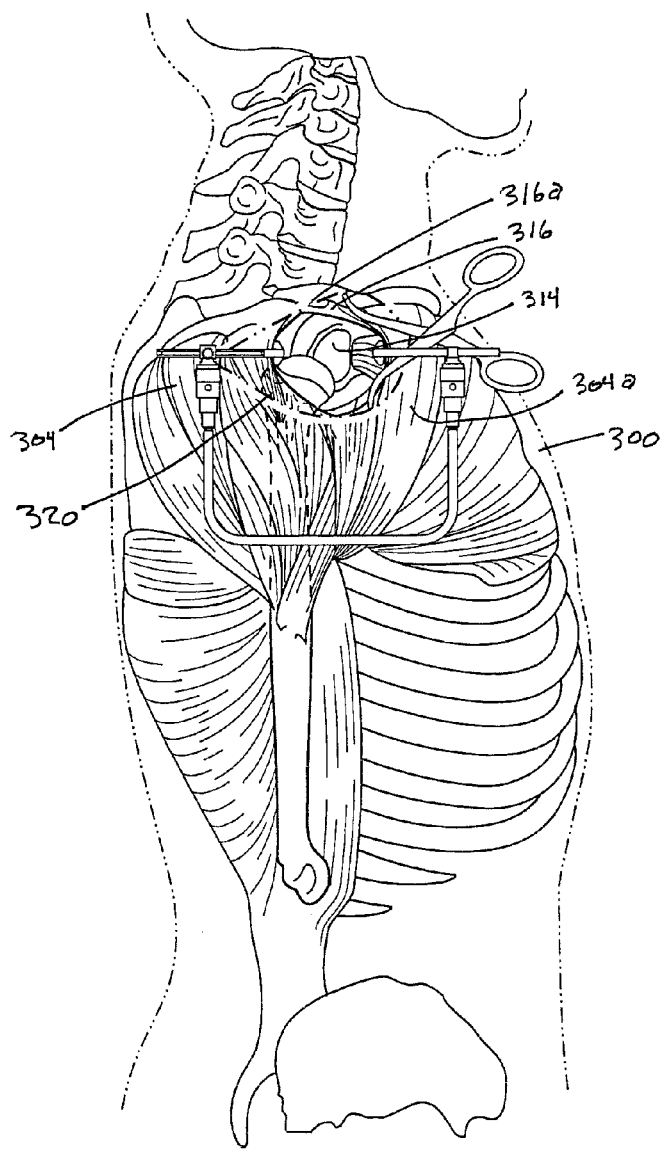
FIGS. 16-19 depict the preparation of the human anatomy to accept the implants of FIGS. 1-15.
Figure 20A:
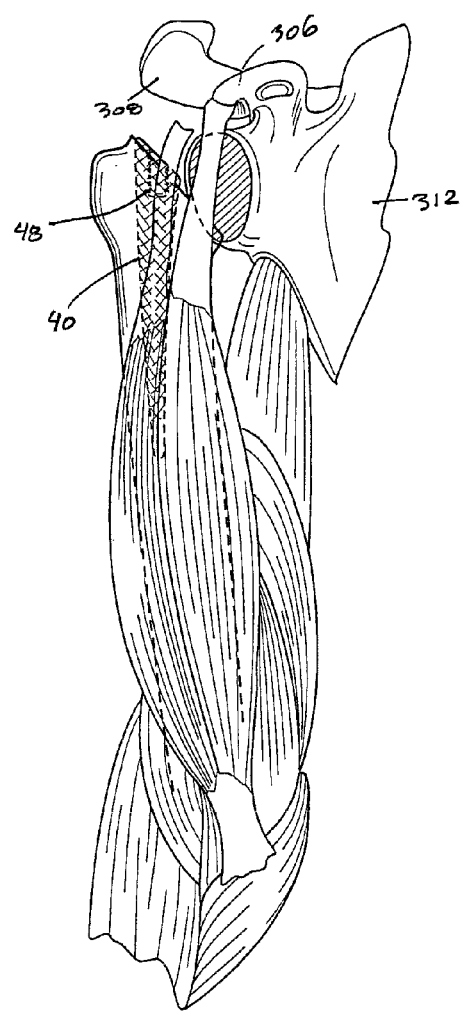
FIGS. 20a and 20b represent the implantation of the stem shown in FIG. 1 and the glenoid of FIG. 14.

With initial reference to FIGS. 16 and 20a, a human anatomy 300 can be augmented with the use of the instruments. The human anatomy 300 generally includes an external skin layer and soft tissue there below, such as muscle 304. Various portions of the anatomy, including the humerus 310 and the glenoid 314, can be accessed by forming an incision 316 in the soft tissue, including the skin.

Also, various subdermal portions, such as subdermal adipose tissue, can be incised along the incision 316. It will be understood that the incision 316 can be orientated in any appropriate direction such as anterior to posterior, which is generally parallel to a sagittal plane. In this regard, the incision is about 5 cm in length. Alternatively, or in addition thereto, a superior-inferior incision illustrated in phantom 316a, which is generally along the coronal plane, can be made. The skin incision can made parallel with Langerhan's lines at the superior aspect of the shoulder, just even with the lateral border of the acromion 306. The incision 316 can also be medialized slightly. The incision 316 can be any appropriate length, and may depend upon surgeon preference, patient type, prosthetics to be used, or other indications. Nevertheless the incision can be about 3 cm (about 1 in) to about 20 cm (8 in) in length such as about 7.5 cm (about 3 in) to about 10 cm (4 in). It will be understood that the incision 316 through the skin may be shorter than the area opened in the muscle 304. The incision 316 can be used to achieve access to the muscle 304 that is around the various portions of the anatomy that are selected to be resected, including the humerus 310 and the glenoid 314. The incision can be used to obtain access to a deltoid muscle 304a.

The retractor can be any appropriate retractor such as a Gelpi Style Retractor. It will be understood that the retractor may also be used to retract the soft tissue, such as the muscles surrounding the glenohumeral joint, including the deltoid muscle 304a, but the Gelpi Style Retractor may also be used to expand the incision 316 to gain access to the muscle. The retractor 60, as illustrated herein, can be used to retract or position the deep tissue that is generally near the glenohumeral joints.

The passage 320 through the deltoid 304a can achieve access to various deeper soft tissue portions, such as the sub-deltoid bursa and the subacromial bursa without damaging the rotator cuff. Further, various other deep soft tissue can be incised and/or moved to achieve access to the capsule surrounding the shoulder or glenohumeral joint. After moving and/or incising all of these portions, access to the humerus 390 or the humeral head 310a can be achieved.

The retractor can be used to hold the various soft tissues portions open, such as the cuff interval, capsule and the like. It will be understood that the retractor may be any appropriate retractor and may include a scissor retractor or the like. Various other soft tissue portions may be near the capsule and may also be incised or resected. For example, the bicep tendon that interconnects to a portion or near the humeral head 310a may be resected or may be moved, if already detached, to achieve better access to the humeral head 310a. Further, access to the glenoid 314 can also be seen once the soft tissue has been incised.

Although the incision 316 on the shoulder or near the glenohumeral joint allows access to the deltoid muscle 304a and access to the capsule and soft tissue surrounding the glenohumeral joints, various muscles and ligaments need not be resected or incised when obtaining access to the glenohumeral joint according to the process discussed herein. For example, the subscapularis muscle and the ligaments attaching it to the portions of the glenohumeral joint need not be incised when obtaining access to the glenohumeral joint according to embodiments of the teachings herein. The subscapularis muscle can be left intact because it is generally anterior from the approach described. Also the supraspinatus can remain intact, as may all the muscles of the rotator cuff. Rather the passage 320 can be formed by separating the cuff interval rather than detaching or incising various soft tissue portions. Further, the humeral head 310a need not be substantially dislocated or dislocated at all from the glenohumeral joint according to various embodiments. Rather, the humeral head 310a can be moved to allow access to various portions of the anatomy, however, major dislocation of the humeral head 310a from the glenoid 314 is not necessary. The humerus can be left in its generally anatomical position or retracted any appropriate distance, such as about 2 cm to about 8 cm.

The soft tissue over the biceps laterally is sharply dissected off the humerus down to the top of the subscapularis tendon, but the tendon can be left undisturbed. The supraspinatus may be stripped back off the anterior portion of the greater tuberosity for a distance of about 5 mm to about 10 mm to further enhance the exposure. More than about 1 cm may not be detached, and the basic integrity of the tendon can remain. This exposure of the rotator interval typically gives about a 1.5 cm to about 2 cm gap at the lateral edge, without disrupting the rotator cuff mechanism. The Gelpi retractor 60a can be moved from the deltoid 304a to the rotator interval and this can provide greater exposure of the glenohumeral joint for instrumentation and implants.

Figure 17:
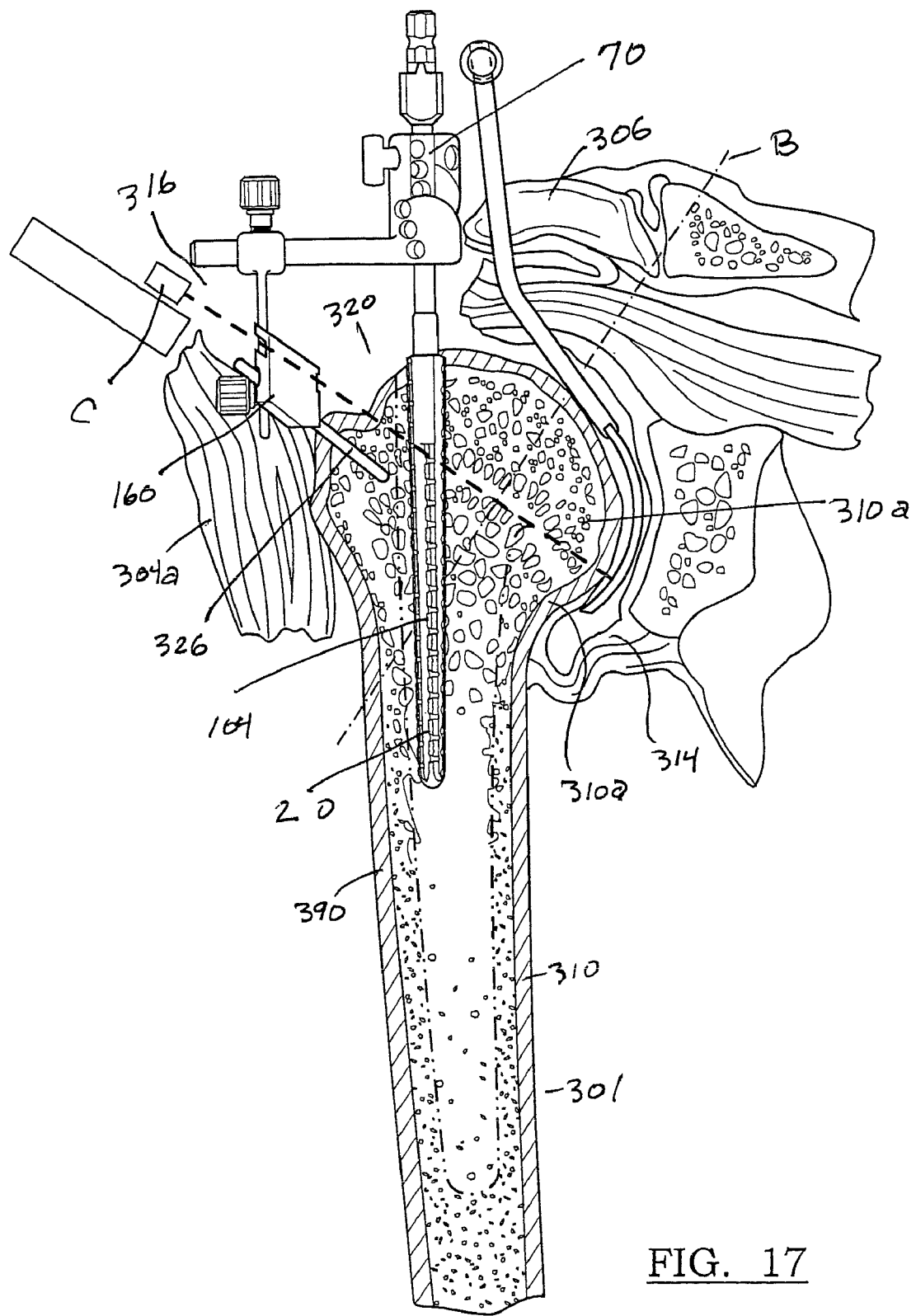

Once access has been obtained to the glenohumeral joint, various instruments according to various embodiments can be used in the procedure. It will be understood that according to various embodiments, any, all, or none of the instruments may be used in a procedure. With reference to FIG. 17 (detailed view of the glenohumeral joint), the reamer 20 can be reamed into the humerus 310 near the humeral head 310a. Humeral reaming can occur from the superior, lateral humeral head. The entrance to the head 310a can be just underneath the previous location (i.e. the natural location) of the biceps tendon. The arm 301 can be extended slightly, and the elbow can be placed against the patient's side to bring the top of the humeral head 310a forward, and allow the reamer to pass the front of the acromion 306. This can allow the humeral head 310a to be retracted, but remain substantially or completely undislocated. This can reduce trauma in the surrounding soft tissue. The superior approach allows easy centering of the reamer in the humeral head and proximal shaft, and decrease the initial incidence of varus stem placement and/or eccentric head utilization.

The reamer 20 includes the shaft 104 that can extend from the humerus 310. The reamer 20 can be positioned into the humerus and interconnected with various portions, such as the guide apparatus 70. The guide apparatus 70 can be interconnected with the shaft 104 of the reamer 20 while the reamer remains in the humerus 310. This allows for positioning the cutting guide 160 relative to the humerus 310 and the humeral head 310a.

The various portions of the apparatus 70, including the guide movement arm, can be used to orient the cutting guide 160 in a proper orientation relative to the humeral head 310a. Generally, it is selected to obtain or position an axis of the cutting guide 160, such as a central axis, relatively in line with the humerus 310. This can help position the guide surface generally perpendicular to an axis B of the humeral head 310a. The axis B is generally about perpendicular to a plane or line C that extends through the humeral head 310a occurs on this plane or line C.

The cutting guide 160 can generally be positioned at about 20 degrees to about 30 degrees of retroversion. Once the cutting guide 160 is positioned in a selected position, it may be held in place with a fixation pin 326. It will be understood that more than one of the fixation pins 326 can be provided and pass through the bores 186, defined by the guide 160. The pins can include any appropriate type of pin and can be drilled into the humerus 310 to hold the cutting guide 160 relative thereto. The various other portions of the guide apparatus, including the guiding arm 172 and the fixation arm 170 can then be removed from the reamer 20. In addition, the reamer 20 can be removed from the humerus to allow for a resection of the humeral head 310a.

The cutting guide 160 can be held in place with the pin 326 when all the other portions of the apparatus are removed. The saw can then be used to resect the humeral head and the blade can ride along a portion of the cutting guide 160. The cutting guide 160 can insure a proper orientation and/or position of the saw blade relative to the humeral head 310. Further, a glenoid shield can be positioned relative to the glenoid 314 and other portions of the anatomy to assist in ensuring that the saw 200 does not engage portions of the anatomy not desired to be cut.

It will be also understood that the cut of the glenoid head 310a can be begun with the cutting guide 160 and then finished without the cutting guide 160. For example, an initial portion of the humeral head 310a can be resected with use of the cutting guide 160. After an initial portion of the cut is formed the cutting guide 160 and the fixation pins 326 can also be removed. The remainder of the cut of the humeral head 310a can then be performed using the initial portion of the cut formed with the saw blade to guide the remaining portion of the cut. Therefore, it will be understood, that the cutting guide 160 need not be present to form the entire cut of the glenoid head 310a.

The glenoid condition can also be assessed, and a decision can be made for hemiarthroplasty or total shoulder arthroplasty. The glenoid is well visualized, and directly approached, as the surgical exposure is lateral as compared to other techniques. Glenoid version, glenoid erosions, and glenoid osteophytes are all easily assessed. Labral tissue is cleared from around the margins, and glenoid preparation can be carried out with a selection of straight reamers and drills. As described below, a keeled or pegged glenoid implant can be utilized, per the surgeon's preference as discussed herein. Although the procedure can proceed according to any appropriate technique, glenoid preparation and implantation can occur prior to humeral broaching, but the humerus could be prepared first if desired.

Figure 18:
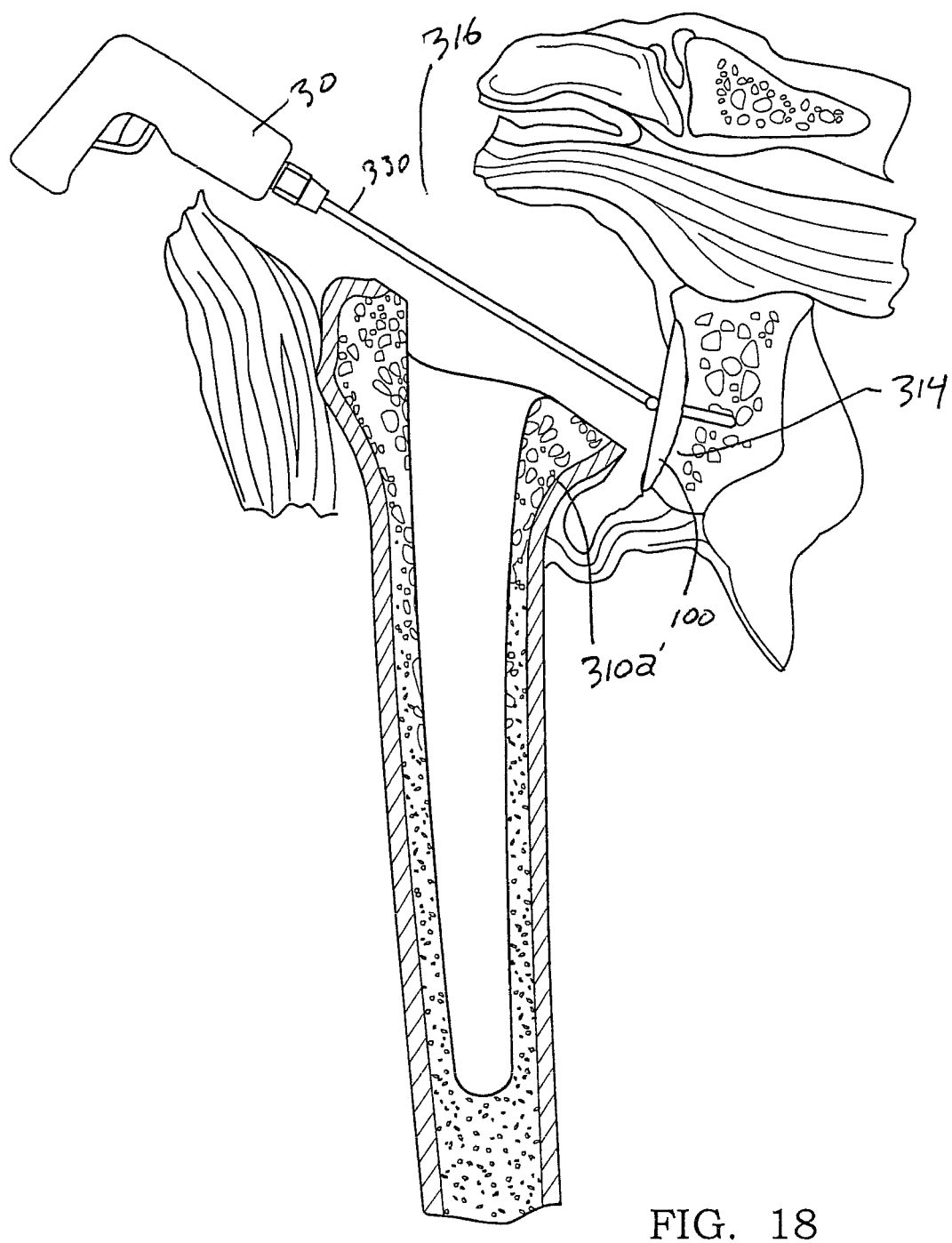

With reference to FIG. 18, once the humeral head 310 has been resected, thus forming the resected humeral head 310a', the glenoid 314 can be reamed with reamer 100. It will be understood that the glenoid 314 may be first prepared with the various procedures according to those commonly known in the art. Nevertheless, it will be understood that the various guides, such as those described herein, can be used to assist in achieving these procedures. As discussed above, various connecting portions can be positioned at a superior or top portion of the sizer or other instrument to assist in achieving the superior approach described herein. The reamer 100 can be interconnected with a reamer shaft 330 and a drill motor 30. This allows the reamer 100 to be rotated relative to the glenoid 314 to form the glenoid into a selected shape and orientation. The glenoid 314 may need to be shaped to allow for implantation of a selected glenoid implant. Nevertheless, it will be understood that the glenoid 314 need not necessarily be resected and may articulate with an implant positioned in the resected humerus 310.

Regardless, the reamer 100 can be positioned relative to the glenoid 314 and the shaft 313 extend through the incision 316 to allow for interconnection with the drill motor 30. After a selected period of reaming, the glenoid 314 can be prepared for implantation of a glenoid implant. As discussed above, the glenoid template 80 can be positioned relative to the reamed glenoid 314 to assist in further glenoid preparation.

Figure 19:
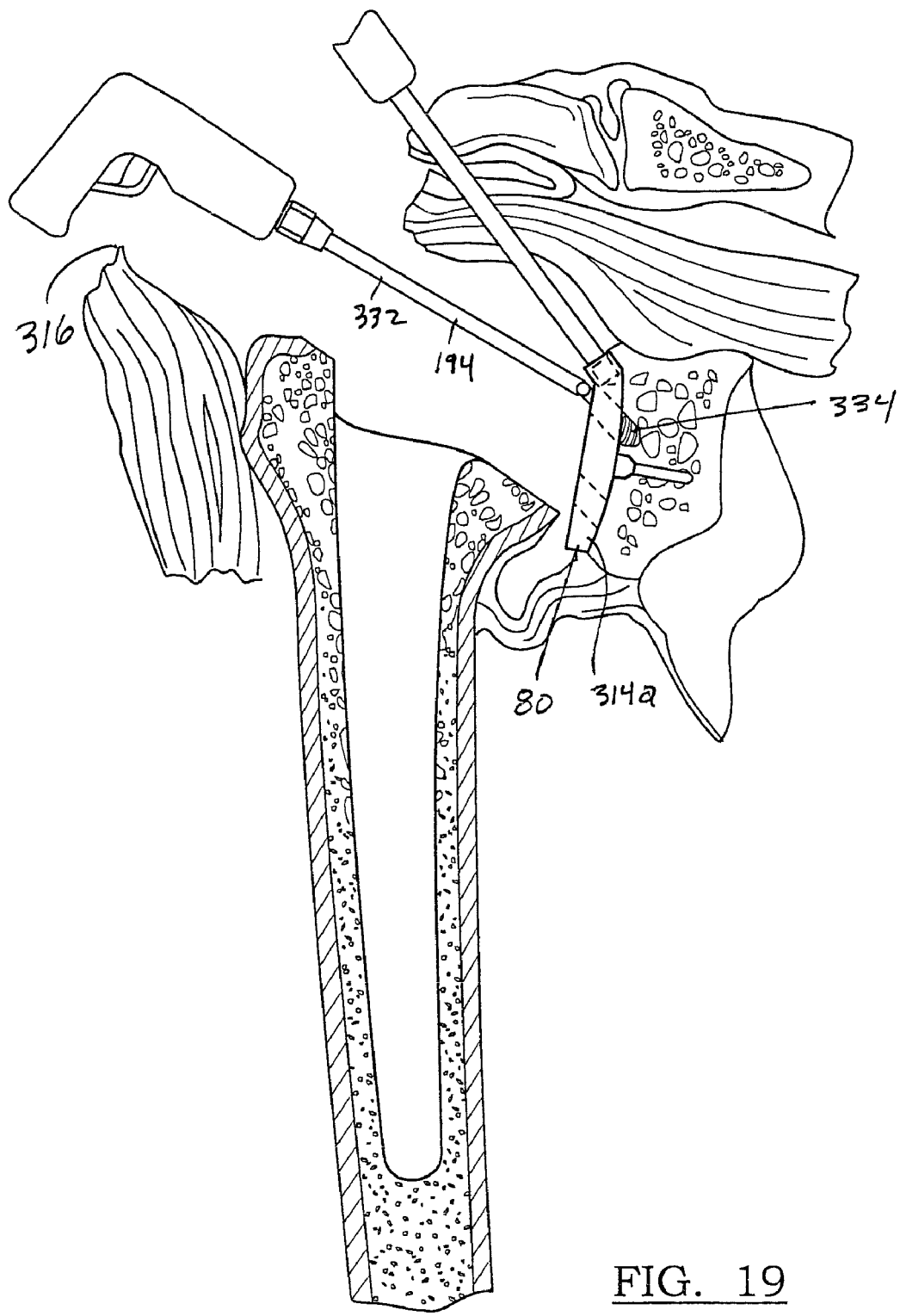

With reference to FIG. 19, the glenoid template 80 can be positioned relative to the reamed glenoid 314a. The guide 80 allows for drilling or forming a plurality of bores in the resected glenoid 314a with a bit 334 that can be interconnected to the drill motor 30 with a shaft 332. The various bores formed in the resected glenoid 314a allow for interconnection and positioning of portions of a glenoid implant, such as pegs extending therefrom, into the glenoid 314. The pegs can be used to resist various motions of the glenoid implant, such as rotation, translation and the like. Further, the pegs allow for cementation points to cement the glenoid implant to the glenoid 314, if selected. Regardless, the guide 80 can be used relative to the glenoid 314 to form various bores, openings, and the like in the glenoid 314.

Once the various bones of the anatomy have been resected, including the glenoid 314 and the humerus 310, the various implants can be implanted. The humerus 310 may need to be further prepared, such as broaching the IM canal of the humerus 310. Therefore, a broach may be provided and used to broach a selected portion of the IM canal of the humerus 310. Various sizes of broaches may be used to progressively enlarge the broached area of the humerus 310, as is generally known in the art.

After inserting the stem 40, 42 or 44 into the medullary canal using impaction, the humeral head 60 is coupled to the locking taper formed on the stem proximal end 50. The coupling mechanism 52 of the humeral head 60 is aligned within the patient to place the central stem axis 46' with the central stem axis 46 of the stem 40. An impact force is applied to the stem in a direction of the coupling mechanism central stem axis 46'. As can be seen in the figures, this axis is substantially not in line with the axis defining the curved articulating surface of the head 60.

Figure 20B:
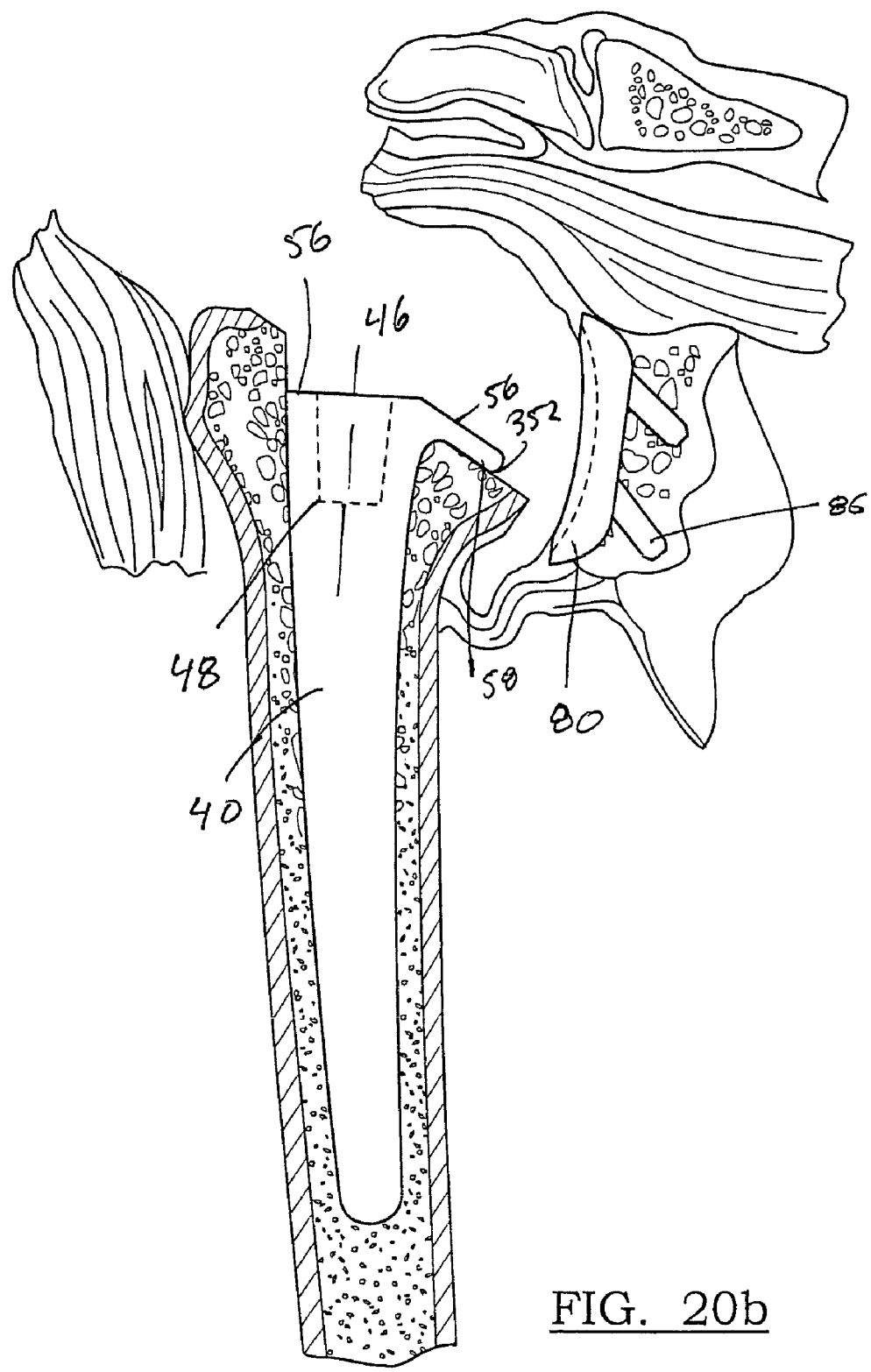
Figure 21:
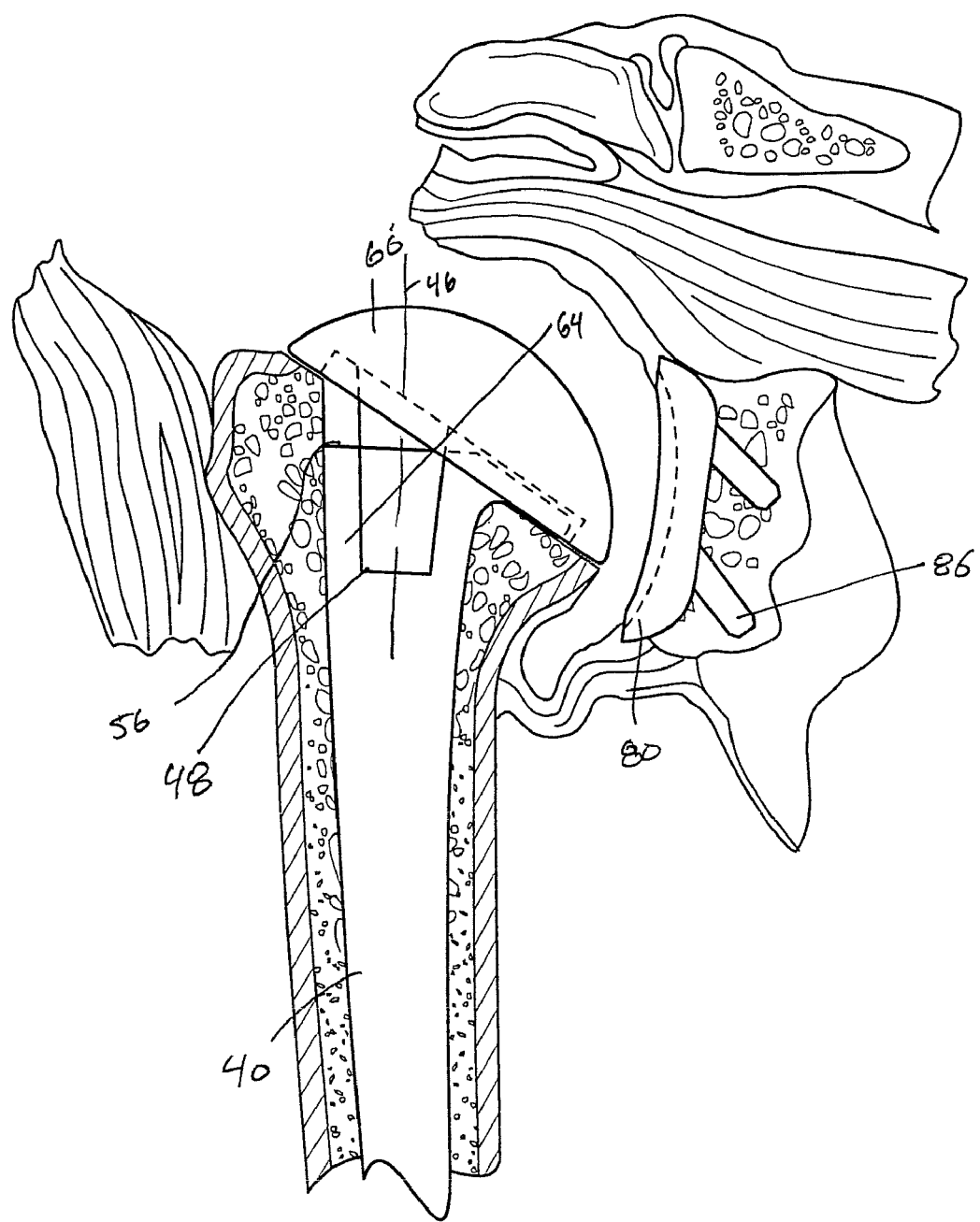
FIG. 21 shows the coupling of the head shown in FIG. 10 to the stem shown in FIG. 2.

FIGS. 20a and 20b represent cross-sectional views of an inserted humeral stem and glenoid prosthetic as shown in FIGS. 4 and 14. It is specifically envisioned that the physician can use a trailing head (66' of FIG. 21) to determine the proper articulation of the shoulder joint. Once the proper head size is determined, the prosthetic head 60 can be permanently coupled to the stem 42. Once the head is positioned, impact forces are imparted onto the head along the central axis 46, coupling the head 60 to the stem 42.

Figure 22:
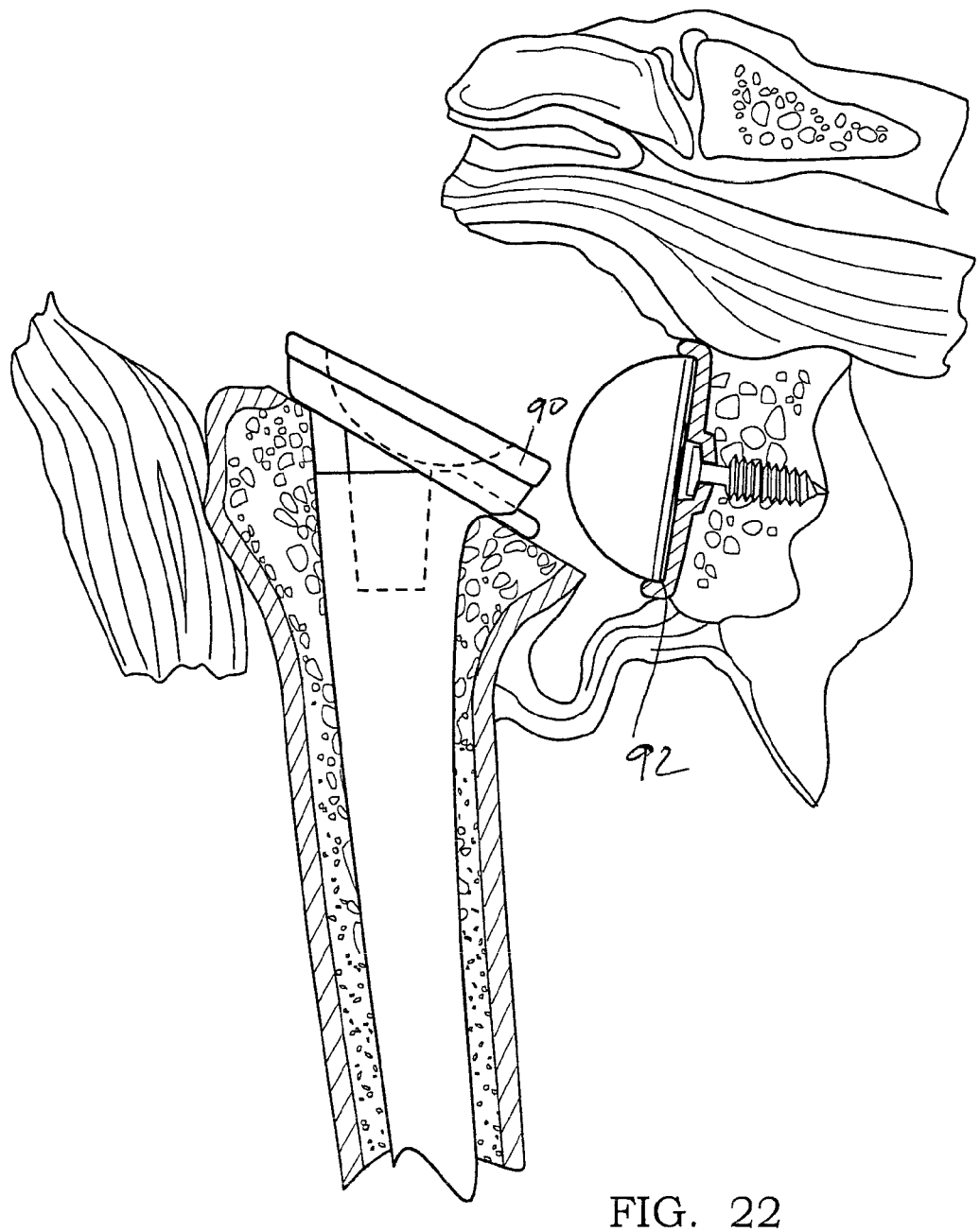
FIG. 22 represents the stem according to FIG. 2 used in a reverse shoulder application.

As shown in FIG. 22, the superior approach can be used to implant a reverse shoulder prosthetic. In this regard, the proximal end of the stem 42 can have a cup member 90 configured to couple to a spherical glenoid implant 92 positioned at a resected glenoid. It is envisioned the cup member 90 can have a fixation member having central axis 46 as previously described.

Following implantation, the soft tissue balance can again be assessed, and then the split in the rotator interval can be closed. The deltoid can be repaired back to the acromion. Subcutaneous tissues and skin can then be closed per the surgeon's usual routine.

Various portions described herein can be provided in a kit. The kit can include any appropriate portions that can be used in a selected procedure, such as a glenoid and/or humeral procedure and can include a plurality of the broaches, a plurality of the humeral implants, a plurality of humeral heads, a plurality of the glenoid implants, and any other appropriate portion. Therefore, the kit can be used for a plurality of procedures and need not be customized for a particular procedure or patient. Further, the kit can include a plurality of portions that allow it to be used in several procedures for many differing anatomies, sizes, and the like. Further, various other portions, such as the reamer, the glenoid template, or other appropriate portions can be provided for a plurality of different patients.

The description is merely exemplary in nature and, thus, variations that do not depart from the gist of the teachings are intended to be within the scope of the teachings. Such variations are not to be regarded as a departure from the spirit and scope of the teachings.

What is claimed is:

1. A method of performing an arthroplasty on at least one of a glenoid, or humeral head of a humerus through soft tissue of an anatomy, comprising:
    forming an entry incision, at a superior-lateral portion of the glenohumeral joint;
    forming a passage from the incision through at least the deltoid muscle substantially superior and lateral of the glenohumeral joint;
    reaming the humerus from the superior, lateral humeral head without dislocating the humeral head from the glenoid;
    resecting the humeral head while the humeral head is located within the glenoid;

inserting a prosthetic stem into an intramedullary canal of the humerus through the incision and the passage;

positioning the prosthetic stem having a central stem axis and a coupling mechanism aligned with the central stem axis within the humerus such that the central stem axis is substantially aligned with a longitudinal axis of the intramedullary canal;

inserting a prosthetic humeral head through the incision and the passage; and coupling the prosthetic humeral head to the coupling mechanism after the stem is inserted into the humerus;

wherein at least one of the subscapularis muscle or supraspinatous muscle remains intact and completely connected to surrounding bone during the entire arthroplasty procedure.

2. The method of claim 1, wherein forming a passage through the deltoid muscle allows access to the at least one of a capsule or a rotator cuff surrounding the humeral head.

3. The method of claim 1, wherein the humeral head comprises a second coupling mechanism configured to be aligned with the central stem axis.

4. The method of claim 3, wherein coupling the head comprises impacting the head at an angle parallel to the stem central stem axis.

5. The method of claim 1, comprising disposing an interface member between the head and the stem.

6. The method of claim 5, wherein the interface member comprises first and second coupling tapers.

7. The method of claim 3, wherein coupling the head to the stem is coupling the head less than 2 mm from the stem.

8. The method of claim 1, further comprising resecting the glenoid.

9. The method of claim 8, further comprising implanting a glenoid implant in the resected glenoid.

10. A method of performing an arthroplasty on a humeral head of a humerus through soft tissue of an anatomy, comprising:

forming an incision in the soft tissue near a glenohumeral joint; prior to resecting the humeral head, reaming the humerus from the superior, lateral humeral head without dislocating the humeral head from the glenoid;

resecting the humeral head while the humeral head is in cooperation with a glenoid of the glenohumeral joint;

positioning within an intramedullary canal of the humerus a prosthetic stem having a central stem axis and a first coupling mechanism having a first coupling axis that is coaxially aligned with the central stem axis, the prosthetic stem is positioned such that the central stem axis is approximately parallel to a longitudinal axis of an intramedullary canal of the humerus; and coupling a prosthetic head to the prosthetic stem after the stem is positioned within the humerus by mating the first coupling mechanism with a second coupling mechanism of the prosthetic head such that:

the first coupling axis is coaxially aligned with a second coupling axis of the second coupling mechanism; and a central axis of the articulating surface of the prosthetic head is not parallel to, or coaxial with, either the first coupling axis or the second coupling axis; wherein at least one of the subscapularis muscle or supraspinatous muscle remains intact and completely connected to surrounding bone during the entire arthroplasty procedure.

11. The method of claim 10, wherein the head defines a stem bearing surface that is substantially perpendicular to the central axis of the articulating surface.

12. The method of claim 10, wherein coupling the head comprises impacting the head along the second coupling axis.

13. The method of claim 10, comprising disposing an interface member between the head and the stem.

14. The method of claim 13, wherein the interface member comprises first and second offset coupling tapers.

15. The method of claim 14, wherein coupling the head to the stem is coupling the head less than about 2mm from the stem.

16. The method of claim 10, further comprising resecting a glenoid.

17. The method of claim 16, further comprising implanting a glenoid prosthetic in the resected glenoid.

18. The method of claim 17 wherein the glenoid prosthetic comprises an articulating surface and an interface surface, said interface surface having a plurality of coupling pegs which engage the surface at a predetermined angle.

19. A method of performing an arthroplasty on a humeral head of a humerus through soft tissue of an anatomy, comprising:

forming an incision in the soft tissue near a glenohumeral joint; prior to resecting the humeral head, reaming the humerus from the superior, lateral humeral head without dislocating the humeral head from the glenoid;

resecting the humeral head while the humeral head is in cooperation with a glenoid of the glenohumeral joint;

positioning a prosthetic stem having a central stem axis and a first coupling mechanism generally aligned with the central stem axis within an intramedullary canal of the humerus such that the central stem axis is approximately parallel to a longitudinal axis of an intramedullary canal of the humerus; and coupling a humeral head to the first coupling mechanism after the stem is inserted into the humerus;

wherein the humeral head comprises an articulating surface with a head central axis extending through an axial center thereof and a planar coupling surface that lies in a plane that is perpendicular to the head central axis, said planar coupling surface having a second coupling mechanism with a central coupling axis that is non-orthogonal to the coupling surface;

wherein at least one of the subscapularis muscle or supraspinatous muscle remains intact and completely connected to surrounding bone during the entire arthroplasty procedure.

20. The method of claim 19, wherein the second coupling mechanism is configured to be aligned with the central stem axis.

21. The method of claim 19, wherein coupling the head to the stem is coupling the head less than about 2 mm from the stem.

22. The method of claim 19, further comprising resecting a glenoid and implanting a glenoid implant in the resected glenoid.

* * * * *

UNITED STATES PATENT AND TRADEMARK OFFICE
CERTIFICATE OF CORRECTION

PATENT NO. : 8,157,866 B2  Page 1 of 1
APPLICATION NO. : 11/934917
DATED : April 17, 2012
INVENTOR(S) : Nathan A. Winslow et al.

It is certified that error appears in the above-identified patent and that said Letters Patent is hereby corrected as shown below:

Column 2,
Line 17, replace "afore mentioned" with --aforementioned--

Column 5,
Line 21, replace "tissues" with --tissue--

Column 9,
Lines 24-25, replace "stem central stem axis" with --central stem axis--

Column 9,
Line 50, replace "an" with --the--

Column 9,
Line 58, replace "of the articulating surface" with --of an articulating surface--

Signed and Sealed this
Thirty-first Day of July, 2012

David J. Kappos
*Director of the United States Patent and Trademark Office*